(12) United States Patent
Bonelli et al.

(10) Patent No.: US 9,358,224 B2
(45) Date of Patent: *Jun. 7, 2016

(54) PHARMACEUTICAL FORMULATION COMPRISING A PHOSPHODIESTERASE INHIBITOR

(75) Inventors: Sauro Bonelli, Parma (IT); Elena Losi, Parma (IT); Enrico Zambelli, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 35 days.

This patent is subject to a terminal disclaimer.

(21) Appl. No.: 13/195,903

(22) Filed: Aug. 2, 2011

(65) Prior Publication Data
US 2012/0034172 A1 Feb. 9, 2012

(51) Int. Cl.
| | |
|---|---|
| *A61K 9/12* | (2006.01) |
| *A61K 31/435* | (2006.01) |
| *C07D 211/82* | (2006.01) |
| *A61K 31/44* | (2006.01) |
| *A61K 9/00* | (2006.01) |

(52) U.S. Cl.
CPC .............. *A61K 31/44* (2013.01); *A61K 9/008* (2013.01); *A61K 9/0078* (2013.01)

(58) Field of Classification Search
CPC ...... A61K 31/44; A61K 9/0078; A61K 9/008
See application file for complete search history.

(56) References Cited

U.S. PATENT DOCUMENTS

| | | | |
|---|---|---|---|
| 7,671,066 B2 | 3/2010 | Amari et al. | |
| 7,820,698 B2 | 10/2010 | Rizzi et al. | |
| 7,923,565 B2 | 4/2011 | Delcanale et al. | |
| 7,968,724 B2 | 6/2011 | Armani et al. | |
| 8,203,000 B2 | 6/2012 | Delcanale et al. | |
| 8,440,834 B2 * | 5/2013 | Amari et al. | 546/339 |
| 2005/0085445 A1 * | 4/2005 | Muller et al. | 514/58 |
| 2005/0089478 A1 * | 4/2005 | Govind et al. | 424/46 |
| 2007/0286814 A1 * | 12/2007 | Sawant et al. | 424/45 |
| 2009/0048220 A1 * | 2/2009 | Delcanale et al. | 514/171 |
| 2010/0129363 A1 * | 5/2010 | Zeldis et al. | 424/133.1 |
| 2010/0204256 A1 | 8/2010 | Amari et al. | |
| 2011/0144075 A1 | 6/2011 | Delcanale et al. | |
| 2012/0031403 A1 | 2/2012 | Cocconi et al. | |
| 2012/0116091 A1 | 5/2012 | Delcanale et al. | |
| 2013/0012487 A1 * | 1/2013 | Amari et al. | 514/171 |

FOREIGN PATENT DOCUMENTS

| | | |
|---|---|---|
| EP | 2 070 913 | 6/2009 |
| EP | 2 216 327 | 8/2010 |
| WO | 2006/131452 | 12/2006 |
| WO | 2009/018909 | 2/2009 |

OTHER PUBLICATIONS

European Search Report in 10171734.6 issued Jan. 18, 2011.
U.S. Appl. No. 14/820,939, filed Aug. 7, 2015, Cocconi, et al.

* cited by examiner

*Primary Examiner* — Mina Haghighatian
(74) *Attorney, Agent, or Firm* — Oblon, McClelland, Maier & Neustadt, L.L.P.

(57) ABSTRACT

Pharmaceutical formulations to be administered by pressurized metered dose inhalers (pMDIs), comprising a compound of general formula (I) may be used for the treatment and/or prevention of inflammatory or obstructive airway diseases.

15 Claims, No Drawings

PHARMACEUTICAL FORMULATION COMPRISING A PHOSPHODIESTERASE INHIBITOR

CROSS REFERENCES TO RELATED APPLICATIONS

This application is claims priority to European Patent Application No. 10171734.6, filed on Aug. 3, 2010, which is incorporated herein by reference in its entirety.

BACKGROUND OF THE INVENTION

1. Field of the Invention

The present invention relates to pharmaceutical formulations to be administered by pressurized metered dose inhalers (pMDIs) or nebulizers. The present invention also relates to processes for the preparation of such a formulation and to a pressurized metered dose inhalers or single or multidose dose vials for nebulizers filled with such a pharmaceutical formulation.

2. Discussion of the Background

Airway obstruction characterizes a number of severe respiratory diseases including asthma and chronic obstructive pulmonary disease (COPD). Events leading to airway obstruction include edema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, avoiding any systemic side-effects, thus providing a more rapid clinical response and a higher therapeutic ratio.

Inhaled corticosteroids are the current maintenance therapy of choice for asthma and together with bronchodilator $\beta_2$-agonists for acute symptom relief, they form the mainstay of current therapy for the disease. The current management of COPD is largely symptomatic by means of bronchodilating therapy with inhaled anticholinergics and inhaled $\beta_2$-adrenoceptor agonists. However, corticosteroids do not reduce the inflammatory response in COPD as they do in asthma.

Another class of therapeutic agents which is under investigation in view of its anti-inflammatory effects for the treatment of inflammatory respiratory diseases such as asthma and COPD is represented by the inhibitors of the phosphodiesterase enzymes (PDEs), in particular of the phosphodiesterase type 4 (hereinafter referred to as PDE4).

Various compounds acting as PDE4 inhibitors have been disclosed. However, the usefulness of several PDE4 inhibitors of the first generation such as rolipram and piclamilast has been limited because of their undesirable side effects such as nausea, gastric acid secretion and emesis due to their action on PDE4 in the central nervous system and due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see Jacobitz, S et al., Mol. Pharmacol., 1996, 50, 891-899, which is incorporated herein by reference in its entirety), which is found in the immune and inflammatory cells. While both forms appear to exhibit catalytic activity, they differ with respect to their sensitivity to inhibitors. In particular, compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as cilomilast and roflumilast. However, even these compounds are not provided with a good selectivity towards LPDE4.

Compounds with selective LPDE4 inhibition activity are disclosed in WO 2009/018909, which is incorporated herein by reference in its entirety.

Additional PDE4 inhibitors having high potency are an object of the co-pending European Patent Application No. PCT/EP2010/000676 (which is incorporated herein by reference in its entirety), wherein it has been surprisingly found that the presence of sulphonamido substituents on the benzoate residue markedly improves the potency and that the (−) enantiomers are more potent than the corresponding (+) enantiomers and racemates.

Therefore, these compounds may provide significant therapeutic benefit in the treatment of respiratory diseases such as asthma and COPD, when administered by inhalation, orally or intranasally.

Thus, there remains a need for formulations for delivering such compounds orally or intranasally or by inhalation.

SUMMARY OF THE INVENTION

Accordingly, it is one object of the present invention to provide novel formulations for delivering a phosphodiesterase inhibitor orally or intranasally or by inhalation.

It is another object of the present invention to provide novel processes for preparing such a formulation.

It is another object of the present invention to provide novel pressurized metered dose inhalers (pMDIs) which contain such a formulation.

It is another object of the present invention to provide novel nebulizers which contain such a formulation.

It is another object of the present invention to provide novel methods of treating and/or preventing certain respiratory diseases by administering such a formulation.

These and other objects, which will become apparent during the following detailed description, have been achieved by the inventors' discovery of certain suspension and liquid formulations which comprise a compound of formula (I).

Thus, the present invention provides pharmaceutical suspension formulations to be administered by pressurized metered dose inhalers (pMDIs) comprising particles of a micronized crystalline compound of general formula (I) or a pharmaceutically acceptable salt thereof and a propellant.

The present invention also provides processes for the preparation of such a formulation The present invention also provides pressurized metered dose inhalers filled with said pharmaceutical formulation.

The present invention also provides a liquid, propellant-free pharmaceutical formulations for administration by nebulization, comprising a compound of general formula (I), dissolved or suspended in water, optionally in presence of one or more co-solvents.

One aim of the present invention is to provide hydrofluoroalkane (HFA) based pressurized metered dose inhaler (pMDI) aerosol compositions that comprise a compound of general formula (I) acting as PDE4 inhibitor, as active ingredient.

Another aim of the present invention is to provide a propellant-free composition for nebulization, comprising a compound of general formula (I) acting as PDE4 inhibitor, to be administered by suitable devices.

Another aim of the present invention is to provide chemically and physically stable aerosol formulations for inhalation of a PDE4 in form of a pMDI or formulation for nebulization.

DETAILED DESCRIPTION OF THE PREFERRED EMBODIMENTS

The present invention provides pharmaceutical formulations to be administered by pressurized metered dose inhalers (pMDIs) or nebulizers, comprising a compound of general formula (I) as (−) enantiomers:

(I)

wherein:
n is 0 or 1;
$R_1$ and $R_2$ may be the same or different, and are selected from the group consisting of:
linear or branched ($C_1$-$C_6$)alkyl, optionally substituted by one or more halogen atoms;
$OR_3$ wherein $R_3$ is a linear or branched ($C_1$-$C_6$)alkyl optionally substituted with one or more halogen atoms or ($C_3$-$C_7$)cycloalkyl groups; and
—$HNSO_2R_4$ wherein $R_4$ is a linear or branched ($C_1$-$C_4$) alkyl optionally substituted with one or more halogen atoms,
wherein at least one of $R_1$ and $R_2$ is —$HNSO_2R_4$,
or a pharmaceutically acceptable salt thereof.

Preferably, the (−) enantiomers are used in a substantially pure form.

The terms "compounds," "active drug," "active ingredient," "active," "active compound," "active substance," and "therapeutic agent" are used synonymously.

The expressions "% w/w" and "% w/v" mean the weight percentage of the component with respect to the total weight or the total volume of the composition, respectively.

By "ethanol anhydrous" it is meant a content of ethanol of not less than 99.5% V/V.

By "daily therapeutically effective dose" it is meant the amount of active ingredient administered at one time by inhalation upon actuation of the inhaler. When administered by pMDIs, said daily dose may be delivered in one or more actuations, preferably one actuation (shot) of the inhaler.

For "actuation" it is meant the release of the active ingredient from the device by a single activation (e.g. mechanical or breath).

The term "substantially pure" means an active ingredient having an optical purity higher than 95% w/w, preferably higher than 98% w/w.

The term "mass median diameter" means the median diameter which divides the mass of particles in two equal parts.

The term "delivered dose" (DD) is calculated from the cumulative deposition in the Andersen Cascade Impactor (ACI) or Next Generation Impactor (NGI) stages, divided by the number of actuations per experiment.

The term "fine particle mass" (FPM) means the total mass of delivered drug recovered on the ACI or NGI stages that capture particles in the respirable particle range (aerodynamic diameter <5 μm).

The aerodynamic diameter is a physical property of a particle in a viscous fluid such as air. In general, particles have irregular shapes with actual geometric diameter that are difficult to measure. Aerodynamic diameter is an expression of a particle's aerodynamic behavior as if it were a perfect sphere with unit-density and diameter equal to the aerodynamic diameter.

The term "fine particle fraction" (FPF) means the percent ratio between the respirable dose and the delivered dose.

The expression "chemically stable formulation" means a formulation wherein the stability and the shelf-life of the active ingredient meet the requirements of the ICH Guideline Q1B, relevant for drug product stability testing for the purposes of drug registration, which is incorporated herein by reference in its entirety.

In the context of the suspension formulations, the expression "physically stable" refers to formulations which exhibit substantially no growth in particle size or change in crystal morphology of the active ingredient over a prolonged period, are readily redispersible, and upon redispersion, do not flocculate so quickly as to prevent reproducing dosing of the active ingredient.

The term "ready-to-use preparation for administration by nebulization" refers to a preparation which is administered directly without further handling and is dispersed in air to form an aerosol by means of a nebulizer, e.g. an instrument that is capable of generating very fine liquid droplet for inhalation into the lungs.

In one aspect, the present invention provides pharmaceutical formulations suitable for aerosol administration by a pMDI, hereinafter referred to as pMDI formulation, comprising a compound of general formula (I) and a propellant.

In a particular embodiment, said pMDI formulation may be in form of suspension of particles of a micronized crystalline compound of general formula (I) in said propellant, so as to permit inhalation of the active ingredient into the lungs upon administration of the aerosol formulation.

Advantageously the particles of the active ingredient shall have a mass median diameter (MMD) of less than 10 micron, preferably in the range of 1 to 10 microns, more preferably 1 to 6 microns.

Any pressure-liquefied propellant may be used, preferably a hydrofluoroalkane (HFA) propellant. Examples of HFA propellants include 1,1,1,2-tetrafluoroethane (HFA134a), 1,1,1,2,3,3,3-heptafluoro-propane (HFA227) and mixtures thereof. In certain embodiments the propellant may consist of HFA 134a, while in other embodiments, the propellant may consist of HFA 227 or a mixture thereof in any ratio.

In a particular embodiment the suspension pMDI formulations may comprise a surfactant, which may also act as a valve lubricant. Suitable surfactants are known in the art and include: sorbitan esters such as sorbitan trioleate, sorbitan monolaurate, sorbitan mono-oleate and their ethoxylated derivates such as polysorbate 20, polysorbate 80; ethylene oxide/propylene oxide co-polymers and other agents such as natural or synthetic lecithin, oleic acid, polyvinylpyrrolidone (PVP), preferably PVP (K25) and polyvinyl alcohol, olive oil, glyceryl monolaurate, corn oil, cotton seed oil or sunflower seed oil, isopropyl myristate, oleyl alcohol, polyoxyethylene

(20) sorbitan monolaurate, polyoxyethylene (20) sorbitan mono-oleate, oleyl polyoxyethylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, glyceryl mono-oleate, glyceryl monostearate, glyceryl monoricinoleate, cetyl alcohol, stearyl alcohol, cetyl pyridinium chloride, ethylene oxide/propylene oxide co-polymer and alcohol ethoxylates such as polyethylene glycol (PEG) 300-1000, diethylene glycol monoethyl ether, Antarox, and Brij.

In a preferred embodiment, the surfactant is PEG 600 or PVP (K25) or a mixture thereof.

The amount of surfactant, which may be present in the pMDI formulation according to the invention, is usually in the range of 0.001 to 3.0% (w/w), preferably 0.005 to 1.0% (w/w), based on the total weight of the formulation.

In a preferred embodiment of the invention, the pMDI formulation may contain a co-solvent. Said co-solvent includes, but it is not limited to polar compounds that contain one or more hydroxyl groups or other polar groups. For example, it includes: an alcohol, such as ethanol, preferably ethanol anhydrous, isopropanol; a glycol such as propylene glycol, polyethylene glycol, polypropylene glycol or glycerol; a glycol ether; and a polyoxyethylene alcohol. Preferably ethanol anhydrous is used in a concentration lower than 20% (w/w), more preferably below 15%, even more preferably 1% to 5% (w/w), most preferably 1 or 5% (w/w).

In other embodiments, the pMDI formulations according to the present invention, may additionally comprise further excipients. Examples of excipients are sugars such as lactose, amino acids such as alanine, betaine, cysteine, and/or antioxidants such as ascorbic acid, citric acid, sodium edetate, editic acid, tocopherols, butylhydroxytoluene, butylhydroxyanisol and ascorbyl palmitate. The weight ratio of the drug to the excipient is generally in the range from 1:0.1 to 1:100.

The pharmaceutical pMDI formulation of the invention may contain at least an active compound selected from the group consisting of C1, C2, C3, C4, C5 and C6, in an amount of 0.02 to 0.7% w/w, preferably 0.05 to 0.5%, ethanol anhydrous in an amount of 1 to 5% w/w, one or more surfactant in an amount of 0.001% to 3% w/w. The propellant is HFA134a or HFA227 or a mixture thereof.

To prepare the suspension pMDI formulation according to the invention, the crystalline compound selected from the group consisting of C1, C2, C3, C4, C5 and C6, is obtained as reported in the co-pending International Patent Application No. PCT/EP2010/000676 (which is incorporated herein by reference in its entirety), is micronized by methods known per se in the art, to prepare the active substance in the form of particles having a typical particle size suitable for inhalation, <3 µm.

According to another aspect, the present invention provides a pMDI comprising a canister filled with a pharmaceutical formulation of the present invention and a metering valve for delivering a daily therapeutically effective dose of the active ingredient.

The pMDI formulation of the invention shall be filled into pMDIs. Said pMDIs comprise a canister fitted with a metering valve. Actuation of the metering valve allows a small portion of the spray product to be released.

Part or all of the internal surfaces of the canister may be made of glass or of a metal, for example aluminum or stainless steel or anodized aluminum.

Alternatively the metal canister may have part or all of the internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene, polyether sulfone and fluorinated-ethylene-propylene polyether sulfone (FEP-PES) mixtures or combination thereof. Other suitable coatings could be polyamide, polyimide, polyamideimide, polyphenylene sulfide or their combinations.

In certain embodiments canisters having the internal surface lined with Teflon may preferably be used. In other particular embodiments canisters made of stainless steel may preferably be used.

The canister is closed with a metering valve for delivering a daily therapeutically effective dose of the active ingredient. Generally the metering valve assembly comprises a ferrule having an aperture formed therein, a body molding attached to the ferrule which houses the metering chamber, a stem constituted of a core and a core extension, an inner- and an outer seal around the metering chamber, a spring around the core, and a gasket to prevent leakage of propellant through the valve.

The gasket may comprise any suitable elastomeric material such as, for example, low density polyethylene, chlorobutyl, black and white butadiene-acrylonitrile rubbers, butyl rubber, neoprene, EPDM (a polymer of ethylenepropylenediene monomer) and TPE (thermoplastic elastomer). EPDM rubbers are particularly preferred.

Suitable valves are commercially available from manufacturers well known in the aerosol industry, for example, from Valois, France, Bespak, plc UK and 3M, Neotechnic Ltd UK.

In general terms the valve seals, especially the gasket seal, as well as the seals shall preferably be manufactured of a material which is inert to and resists extraction into the contents of the formulation, especially when the contents include ethanol.

Advantageously the material of the metering chamber is inert to and may resist distortion by contents of the formulation. Particularly suitable materials for use in manufacture of the metering chamber include acetals and polyesters e.g. polybutyleneterephthalate (PBT).

According to a preferred embodiment of the present invention, the material of all the internal surface of the canister as well as the material of the metering chamber, the core, the core extension, the spring and the body of the valve may be substantially or completely made of a metal, preferably of stainless steel.

Suitable valves are commercially available from manufacturers well known in the aerosol industry, for example, from Valois, France (eg. DF10, DF30, DF31, DF60), Bespak pic, UK (eg. BK300, BK356, BK357) and 3M-Neotechnic Ltd, UK (eg. Spraymiser).

The formulation shall be actuated by a metering valve able of delivering a volume of 25 µl to 100 µl, e.g. 25 µl, 63 µl, or 100 µl.

Advantageously the MDI device filled with the formulation may be equipped with a dose counter.

Conventional bulk manufacturing methods and known machinery may be employed for the preparation of large scale batches for the commercial production of filled canisters. For example, the pMDI suspension formulations according to the present invention may be prepared by adding the active ingredient to a chilled propellant or optionally a pre-mixed blend of propellant and optionally further excipients and, then dispersing the resulting suspension using a suitable mixer. After homogenization, the suspension can be filled into the MDI canister which is closed by crimping a metering valve on the canister.

Alternatively the active ingredient and optionally further excipients can be added to a vessel. The liquefied propellant is then introduced into the vessel under pressure and the active ingredient is dispersed and homogenized using a suitable mixer and homogenizer. After homogenization, the bulk formulation can be transferred into the individual MDI canisters by using valve to valve transfer methods.

Alternatively, the co-solvent, if it is present, is introduced into a vessel at room pressure. The active ingredient and optional further excipients are added and homogeneized using a suitable homogenizer. The ethanolic suspension is kept under stirring. The ethanolic bulk is then dosed into the open canister. The valve is placed onto the can and crimped. Finally, the canister is pressure-filled with the final solution formulation through the valve.

The pMDI formulations according to the present invention, depending on volume of the metering valve to be used, may suitably comprise 0.1 mg to 80 mg of a compound of formula (I) per ml, preferably 0.5 mg re ml to 25 mg per ml.

The pMDI formulations in the form of suspensions comprising particles of a micronized crystalline compound of general formula (I) and a propellant, comprise the active ingredient in an amount such that, in case of administration by inhalation from inhalers, the daily therapeutically effective dose (hereinafter the daily dose) of compound of formula (I) is advantageously 10 µg to 2000 µg, preferably 20 µg to 1000 µg, even more preferably 50 µg to 800 µg, even more preferably 80 to 700 µg, even more preferably 300 µg to 600 µg.

According to a preferred embodiment, the single dose may be 100 to 300 µg, while according to another preferred embodiment, the single dose may be 200 to 800 µg, more preferably 300 to 600 µg.

In further embodiments, the single dose may be 100 µg, 200 µg, 400 µg or 600 µg.

Said dose will depend on the kind and the severity of the disease and the conditions (weight, sex, age) of the patient and will be administered one or more times a day, preferably once a day.

In one embodiment, the daily dose may be reached by a single or double administration.

In another preferred embodiment, the daily dose may be reached by a single administration and delivered in one actuation of the inhaler.

In another preferred embodiment, the daily dose may be reached by a single administration and delivered in more actuations of the inhaler, preferably two.

In another preferred embodiment, the daily dose may be reached by a double administration and delivered in one actuation of the inhaler.

In another preferred embodiment, the daily dose may be reached by a double administration and delivered in more actuations of the inhaler, preferably two.

The daily dose may be delivered in one or two or more actuations (shots) of the inhaler wherein the pharmaceutical composition is contained. For example, a 400 µg daily dose may be administered in one shot of 400 µg or as two shots of 200 µg dose.

In another aspect, the compound of general formula (I) may be dissolved or suspended, to give a nebulizable aqueous solution or suspension, hereinafter referred to as a nebulized formulation, available either as for a single dose or multi-dose vials formulation.

Said nebulized formulation may have the pH and/or tonicity adjusted with suitable buffers and/or isotonic agents, and optionally, it could also comprise stabilizing and/or preserving agents.

In a more preferred embodiment, said nebulized formulation may comprise a solvent.

In a preferred embodiment, said nebulized formulation may comprise a solvent selected from water or an aqueous solution and a co-solvent miscible with water. Said co-solvent includes, but it is not limited to polar compounds that contain one or more hydroxyl groups or other polar groups. For example, it includes alcohols, such as ethanol, ethanol anhydrous, isopropanol and glycols including propylene glycol, polyethylene glycol, polypropylene glycol, glycol ether, glycerol and polyoxyethylene alcohols.

The present invention also provides a single dose or multidose vial filled with said nebulized formulation for delivering a daily therapeutically dose of the active ingredient by a nebulizer.

The liquid, propellant-free pharmaceutical formulation in the form of ready-to-use preparation for administration by nebulization of the present invention, comprises compound of formula (I) in an amount such that the daily dose is advantageously about 35 µg to about 7000, preferably about 70 µg to about 3500 µg, even more preferably about 175 µg to about 2800 µg, even more preferably about 280 µg to about 2100 µg, even more preferably about 350 µg to about 1750 µg.

According to a preferred embodiment, the single dose may be about 350 to about 700 µg, while according to another preferred embodiment, the single dose may be about 700 to about 1400 µg.

In further embodiments, the single dose may be about 350 µg, about 700 µg, or 1400 µg.

The formulation is preferably used as ready-to-use formulation.

However said nebulized formulations may also be realized in a lyophilized form in unitary doses for the reconstitution in a solution. In this alternative embodiment, a single dose of a lyophilized preparation may be reconstituted before use with a solvent vial in a solution.

These nebulized formulations may also be distributed in suitable containers such as multidose vials or, preferably, single dose vials for single dosage administration. Said single-dose vials may be pre-sterilized or, preferably, may be aseptically filled using the "blow, fill and seal" technology. The filling is preferably carried out under inert atmosphere.

Solution formulations can be advantageously sterilized by filtration. The single-dose vials are preferably of 2 ml. For suspension formulations, the sterilization process is carried out through known techniques.

These formulations are intended for administration using suitable nebulizing apparatus such as jet nebulizers, ultrasonic nebulizers, mesh-vibrating nebulizers, soft-mist nebulizers such as Respimat® or others.

Therefore the present invention also provides kits comprising a nebulized formulation provided herein filled in vials for single dosage administration and a nebulizer.

According to a preferred embodiment, the pMDI and nebulized formulations of the present invention comprise a compound of general formula (I), selected from C1, C2, C3, C4, C5 and C6, reported below:

| Compound | Chemical name |
|---|---|
| C1 | (−)-3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester |
| C2 | (−)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester |

-continued

| Compound | Chemical name |
|---|---|
| C3 | (−)-4-Cyclopropylmethoxy-3-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| C4 | (−)-3,4-Bis-methanesulfonylamino-benzoic acid 1-(3-cyclopropyl-methoxy-4-difluoromethoxy-phenyl)-2-(3,5-dichloro-1-oxy-pyridin-4-yl)-ethyl ester |
| C5 | (−)-3-Methanesulfonylamino-4-methyl-benzoic acid 1-(3-cyclopropyl-methoxy-4-difluoromethoxy-phenyl)-2-(3,5-dichloro-1-oxy-pyridin-4-yl)-ethyl ester |
| C6 | (−)-4-Methanesulfonylamino-3-methyl-benzoic acid 1-(3-cyclopropylmethoxy-4-difluoromethoxy-phenyl)-2-(3,5-dichloro-1-oxy-pyridin-4-yl)-ethyl ester |

In one embodiment, the preferred compound of the pMDI formulation or nebulized formulation is C1. In another embodiment, the preferred compound is C2. In further preferred embodiments, the compound might be C3, C4, C5 or C6.

All the pMDI and nebulized formulations of the present invention may further comprise other therapeutic agents currently used in the treatment of respiratory disorders, e.g. corticosteroids such as triamcinolone acetonide, fluticasone propionate, fluticasone furoate, flunisolide, mometasone furoate, rofleponide and ciclesonide; anticholinergic or antimuscarinic agents such as ipratropium bromide, oxytropium bromide, glycopirronium bromide and tiotropium bromide; long-acting $\beta_2$ agonist such as vilanterol, indacaterol, milveterol, salbutamol, levalbuterol, terbutaline, AZD-3199, BI-1744-CL, LAS-100977, bambuterol, isoproterenol, procaterol, clenbuterol, reproterol, fenoterol and ASF-1020 and salts thereof.

The present invention also relates to anyone of the formulations described before, for use as a medicament.

In a further aspect, the present invention provides any one of the formulations described before, for use in the prevention and/or treatment of an inflammatory or obstructive airways disease such as asthma or chronic obstructive pulmonary disease (COPD).

In a further aspect, the present invention provides the use of any one of the formulations described before, in the prevention and/or treatment of an inflammatory or obstructive airways disease such as asthma or chronic obstructive pulmonary disease (COPD).

In a still further aspect, the present invention provides a method of preventing and/or treating an inflammatory or obstructive airways disease such as asthma or chronic obstructive pulmonary disease (COPD), which comprises administration by inhalation of an effective amount of one of the formulations described before.

Administration of any of the formulations of the invention may be indicated for the prevention and/or treatment of mild, moderate or severe acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis may also benefit by this kind of formulation.

Other features of the invention will become apparent in the course of the following descriptions of exemplary embodiments which are given for illustration of the invention and are not intended to be limiting thereof.

EXAMPLES

Example 1

A pharmaceutical aerosol composition was prepared, comprising C2, anhydrous ethanol as co-solvent, PVP (K25) as surfactant and HFA227 propellant, as shown in Table 1.

TABLE 1

| Component | µg/actuation | Quantity |
|---|---|---|
| C2 | 200 | 0.23% w/w |
| Anhydrous Ethanol | 857 | 1.0% w/w |
| PVP (K25) | 86 | 0.1% w/w |
| HFA 227 | 84538 | 98.67% w/w |
| Total | 85681 | 100% w/w |

The efficacy of an MDI device is a function of the dose deposited at the appropriate site in the lungs. Deposition is affected by the aerodynamic particle size distribution of the formulation which may be characterized in vitro through several parameters.

The aerodynamic particle size distribution of the formulation of the invention may be characterized using a Cascade Impactor according to the procedure described in the European Pharmacopoeia $6^{th}$ edition, 2009 (6.5), part 2.09.18, which is incorporated herein by reference in its entirety. An Apparatus E, operating at a flow rate range of 30 l/minute to 100 l/minute or an Apparatus D ACI, operating at a flow rate of 28.3 l/minute may be used. Deposition of the drug on each ACI plate is determined by high performance liquid chromatography (HPLC).

The following parameters of the particles emitted by a pressurized MDI may be determined:

i) mass median aerodynamic diameter (MMAD) is the diameter around which the mass aerodynamic diameters of the emitted particles are distributed equally;

ii) delivered dose is calculated from the cumulative deposition in the ACI, divided by the number of actuations per experiment;

iii) respirable dose (fine particle dose=FPD) is obtained from the deposition from Stages 3 (S3) to filter (AF) of the ACI, corresponding to particles of diameter≤4.7 microns, divided by the number of actuations per experiment; and iv) respirable fraction (fine particle fraction=FPF) which is the percent ratio between the respirable dose and the delivered dose.

Physical and chemical stability of the formulation reported in table 1 has been assessed in a stability study at 1 and 3 months at 25° C./60% relative humidity (RH).

Performances of the formulation reported in Table 1 were characterized using a Next Generation Impactor (NGI).

Chemical stability and performances data of the formulation are reported in Table 2, wherein "mean delivered dose intra-can" means the mean delivered dose of ten actuations on the same can (3 actuations at the beginning, 4 actuations in the middle and 3 actuations at the end of the life of the can).

TABLE 2

|  | | Check points | |
| --- | --- | --- | --- |
| Test | T = 0 | 1 month at 25° C./ 60% RH | 3 months at 25° C./ 60% RH |
| C2 Can content (%) | 100 | 101.1 | 100.6 |
| Total impurities/Degradation products (%) | 1.5 | 1.7 | 1.5 |
| FPM (µg) | 118.7 | 128.4 | 128.2 |
| FPF (%) | 79.3 | 81.4 | 81.3 |
| MMAD (µm) | 2.4 | 2.5 | 2.5 |
| Mean delivered dose intra-can (µg) | 149.72 | 156.88 | 157.7 |
| Uniformity of Delivered Dose intra-can | Complies with the requirement of Ph. Eur. | Complies with the requirement of Ph. Eur. | Complies with the requirement of Ph. Eur. |

NGI sampling flow rate=30 l/minute

The data reported in table 2 show a good chemical stability of C2 (no degradation during stability). The formulation showed good delivered dose uniformity and a high fine particle fraction.

The physical stability of the formulation reported in Table 1 was assessed using Turbiscan® Lab Expert equipment for a time period of 10 minutes. Turbiscan enables to get a quick and objective measurement of the sedimentation behavior of suspension drugs and it is therefore preferred with respect to visual observation. The different instability phenomena (creaming, sedimentation, flocculation, coalescence) can be identified and quantified via different parameters, allowing an objective analysis to be made.

The heart of the optical scanning analyzer, Turbiscan®, is a detection head, which moves up and down along a flat-bottom cylindrical glass cell. The detection head is composed of a pulsed near infrared light source ($\lambda$=880 nm) and two synchronous detectors. Turbiscan can be used in two different modes: backscattering mode or transmission mode. Turbiscan has been used in the reported examples in transmission mode, i.e. to measure the transmitted light as a function of time.

For pressurized systems, a cell capable of handling pressurized samples is required. Such a cell was used for the evaluations of these HFA formulations.

Delta T is the parameter used for the physical characterization of the formulations reported in the examples. Delta T measures the % of variation of light transmitted through the sample in a predetermined range of time. In particular, for the examples here reported, Delta T was measured for a time period of 10 minutes, a time window that widely covers the time needed for patient to use the device. A physically stable suspension has a low value of this parameter (<1%), whilst for unstable suspension this percentage increase significantly. Delta T for the formulation reported in table 1, after 10 minutes, is less than 0.2%, confirming its physical stability.

Example 2

A pharmaceutical aerosol composition was prepared, comprising C2, ethanol anhydrous as co-solvent, PVP (K25) as surfactant and HFA227 propellant, as reported in Table 3.

TABLE 3

| Component | µg/actuation | Quantity |
| --- | --- | --- |
| C2 | 200 | 0.23% w/w |
| Anhydrous Ethanol | 4284 | 5% w/w |

TABLE 3-continued

| Component | µg/actuation | Quantity |
| --- | --- | --- |
| PVP (K25) | 85.68 | 0.1% w/w |
| HFA 227 | 81111 | 94.67% w/w |
| Total | 85681 | 100% w/w |

Performances of the formulation reported in Table 3 were characterized using NGI, and the data are reported in Table 4.

TABLE 4

| Delivered Dose (µg) | Fine Particle Mass (µg) | Fine particle Fraction (%) | MMAD (µm) |
| --- | --- | --- | --- |
| 161.76 | 64.23 | 39.9 | 3.2 |

NGI sampling flow rate=30 l/minute

Delta T for the formulation reported in Table 3, after 10 minutes, is less than 0.2%, confirming its physical stability.

Example 3

A pharmaceutical aerosol composition was prepared, comprising C2, ethanol anhydrous as co-solvent, PVP (K25) as surfactant, PEG600 as surfactant and HFA227 propellant, as reported in Table 5.

TABLE 5

| Component | µg/actuation | Quantity |
| --- | --- | --- |
| C2 | 200 | 0.23% w/w |
| Anhydrous Ethanol | 4284 | 5% w/w |
| PVP (K25) | 85.68 | 0.1% w/w |
| PEG600 | 42.84 | 0.05% w/w |
| HFA227 | 81068 | 94.62% w/w |
| Total | 85681 | 100% w/w |

Delta T for the formulation reported in Table 5, after 10 minutes, is less than 0.2%, confirming its physical stability Example 4

A pharmaceutical aerosol composition was prepared, comprising C2, ethanol anhydrous as co-solvent, PVP (K25) as surfactant and HFA134a propellant, as reported in Table 6.

TABLE 6

| Component | µg/actuation | Quantity |
| --- | --- | --- |
| C2 | 200 | 0.26% w/w |
| Anhydrous Ethanol | 3780 | 5% w/w |
| PVP (K25) | 75.6 | 0.1% w/w |
| HFA 134ea | 71544 | 94.64% w/w |
| Total | 75600 | 100% w/w |

Aerosol Characterization with NGI.

TABLE 7

| Delivered Dose (µg) | Fine Particle Mass (µg) | Fine Particle Fraction (%) | MMAD (µm) |
| --- | --- | --- | --- |
| 167 | 65 | 39 | 2.7 |

NGI sampling flow rate=30 l/min

Delta T for the formulation reported in Table 6, after 10 minutes, is less than 0.2%, confirming its physical stability.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical formulation for aerosol administration, comprising:

(a) the (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester;

(b) a propellant;

(c) a co-solvent; and (d) a surfactant selected from the group consisting of a PEG surfactant, a PVP surfactant, and a mixture thereof.

2. A formulation according to claim 1, which is in the form of suspension.

3. A formulation according to claim 1, wherein said surfactant is selected from the group consisting of PEG 600, PVP (K25), and a mixture thereof.

4. A pharmaceutical formulation according to claim 1, wherein said co-solvent is ethanol.

5. A formulation according to claim 1, which comprises said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl) ethyl ester in an amount of 0.02 w/w to 0.7 w/w, based on the total weight of the formulation.

6. A formulation according to claim 1, wherein said propellant is a hydrofluoroalkane selected from the group consisting of 1,1,1,2-tetrafluoroethane, 1,1,1,2,3,3,3-heptafluoro-n-propane, and a mixtures thereof.

7. A pressurized metered dose inhaler (pMDI), containing a formulation according to claim 1.

8. A method of treating inflammatory or obstructive airway disease, comprising administering an effective amount of a formulation according to claim 1 to a subject in need thereof.

9. A method according to claim 8, wherein said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester is administered at a daily therapeutically effective dose of 10 μg to 2000 μg.

10. A method according to claim 8, wherein said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester is administered at a daily therapeutically effective dose of 20 μg to 1000 μg.

11. A method according to claim 8, wherein said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester is administered at a daily therapeutically effective dose of 50 μg to 800 μg.

12. A method according to claim 8, wherein said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester is administered at a daily therapeutically effective dose of 80 μg to 700 μg.

13. A method according to claim 8, wherein said (–) enantiomer of 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester is administered at a daily therapeutically effective dose of 300 μg to 600 μg.

14. A formulation according to claim 1, which comprises said 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester having an optical purity higher than 95% w/w, based on the weight of said 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester.

15. A formulation according to claim 1, which comprises said 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester having an optical purity higher than 98% w/w, based on the weight of said 3-cyclopropylmethoxy-4-methanesulfonylaminobenzoic acid 1-(3-cyclopropylmethoxy-4-difluoromethoxyphenyl)-2-(3,5-dichloro-1-oxypyridin-4-yl)ethyl ester.

* * * * *